United States Patent [19]

McEachern

[11] 4,106,494
[45] Aug. 15, 1978

[54] HEART DEFIBRILLATING AND MONITORING SYSTEM

[75] Inventor: Robert A. McEachern, Wellesley, Mass.

[73] Assignee: American Optical Corporation, Southbridge, Mass.

[21] Appl. No.: 828,395

[22] Filed: Aug. 29, 1977

[51] Int. Cl.² ............................................. A61B 5/04
[52] U.S. Cl. .......................... 128/2.06 B; 128/2.1 P; 128/419 D
[58] Field of Search ............ 128/419 D, 2.06 B, 2.1 P

[56] References Cited

U.S. PATENT DOCUMENTS

| | | | |
|---|---|---|---|
| 3,653,387 | 4/1972 | Ceier | 128/419 D |
| 3,690,313 | 9/1972 | Weppner et al. | 128/2.06 B |
| 3,814,105 | 6/1974 | Howard et al. | 128/419 D |
| 3,865,101 | 2/1975 | Saper et al. | 128/419 D |
| 4,066,974 | 1/1978 | Reinhard | 128/2.06 B |

*Primary Examiner*—William E. Kamm
*Attorney, Agent, or Firm*—Jeremiah J. Duggan; Stephen A. Schneeberger

[57] ABSTRACT

In a defibrillator/monitor having first electrodes for applying the defibrillating signal and second electrodes for monitoring physiological conditions and switch means for connecting the active leads to the defibrillator monitor through an isolation amplifier the inclusion of additional isolation amplification means intermediate the defibrillating electrodes and the switch means to prevent current leakage between the two electrode systems during the application of the defibrillating signal.

7 Claims, 2 Drawing Figures

HEART DEFIBRILLATING AND MONITORING SYSTEM

BACKGROUND OF INVENTION

The present invention relates to defibrillating and monitoring systems and more particularly to monitoring systems having selective signal inputs by either the defibrillation leads or the conventional patient leads.

Combined heart monitoring and defibrillation systems are known in which a single set of electrodes is utilized both as the ECG pick-up electrodes and as the defibrillation electrodes. With such electrode arrangements, a patient may be first monitored, subsequently have defibrillation pulses applied, and later be monitored again all on the same electrodes. As disclosed in U.S. Pat. No. 3,547,108 issued Dec. 15, 1970 to Seiffert for Combination Defibrillator and Heart Monitoring System, a high voltage transfer relay is provided for isolating the monitoring equipment from the high voltage transient during delivery of a defibrillation pulse.

Transfer relays having the ability to withstand the high transient voltages associated with defibrillation pulses are quite expensive. Likewise, relays are mechanical in nature and subject to mechanical break down. As an alternative to such transfer relays, at least one combined defibrillation-monitoring system has employed an isolation amplifier at the input to the monitoring circuitry (that system being marketed by American Optical Corporation under the registered trademark PULSAR ® 4). Such use of an isolation amplifier serves to substantially reduce the cost of circuit isolation as well as to permit some signal processing, such as filtering, not possible with a transfer relay. In this system there is also provided a separate set of patient electrodes and leads dedicated solely to the ECG monitoring function. That set of patient leads is selectively connected to the input of the isolation amplifier alternatively with the combined defibrillation-monitor leads via a lead selector switch. During defibrillation when high transient potentials appear on the defibrillation leads or other equipment leads, the air around the lead selector switch may break down and conduct, thereby damaging the switch. This occurs when a leakage circuit is created by a conductive foreign object at a different potential contacting either the leads or a floating-ground chassis in such as a battery powered system. Conventionally, neon tubes are used to protect such switches, however, they do not generally prevent these leakage circuits from occurring. Characteristically these tubes break down at a lower voltage (i.e. 80 volts) than the transient high voltages otherwise applied to the selector switch.

Accordingly, it is a principal object of the invention to provide an improved combination defibrillation and monitoring system of the type employing isolation amplifiers for circuit isolation and protection.

SUMMARY OF THE INVENTION

In accordance with the present invention there is provided in a defibrillating and monitoring system having a source of high-voltage defibrillating signals and signal monitoring means for monitoring the signals indicative of heart activity, a first electrode system for selectively applying defibrillating signals to a patient and for selectively applying monitoring signals to the means for monitoring signals, and a second electrode system for selectively applying monitoring signals to the means for monitoring signals, the means for monitoring signals including a first isolation amplifier, a switch means for selectively applying monitoring signals to the first isolation amplifier alternatively from the first electrode system or from the second electrode system, the improvement comprising a second isolation amplifier coupled intermediate the first electrode system and the switch means whereby to prevent current leakage between the first electrode system and the second electrode system. The inclusion of the isolation amplifier intermediate the first electrode system and the switch means is particularly desirable in those defibrillating and monitoring systems which are battery powered and have a floating ground, rather than an intentional direct connection to actual ground or earth potential.

The second isolation amplifier of the improved defibrillating and monitoring system is comprised of three separate mutually conductively isolated sections including an input section having an AC modulator, an output section having a demodulator, and an oscillator section, the modulator being conductively isolated from the demodulator and the oscillator section being conductively isolated from the AC modulator and from the demodulator, thereby to also prevent a current path from the first electrode system through the second electrode system and the second isolation amplifier demodulator section and oscillator section.

The isolation amplifier comprising the improvement of the invention is particularly useful in a heart defibrillating and monitoring system wherein the first electrode system and the second electrode system are each connected to a common guard or shield conductor through respective threshold discharge devices, each threshold discharge device being operative to isolate the respective electrode systems from the common guard conductor only so long as the electrical potential there across is less than a predetermined threshold value, and wherein the predetermined threshold value is substantially less than the potential of the defibrillating signal.

DESCRIPTION OF A PREFERRED EMBODIMENT

Figure 1:
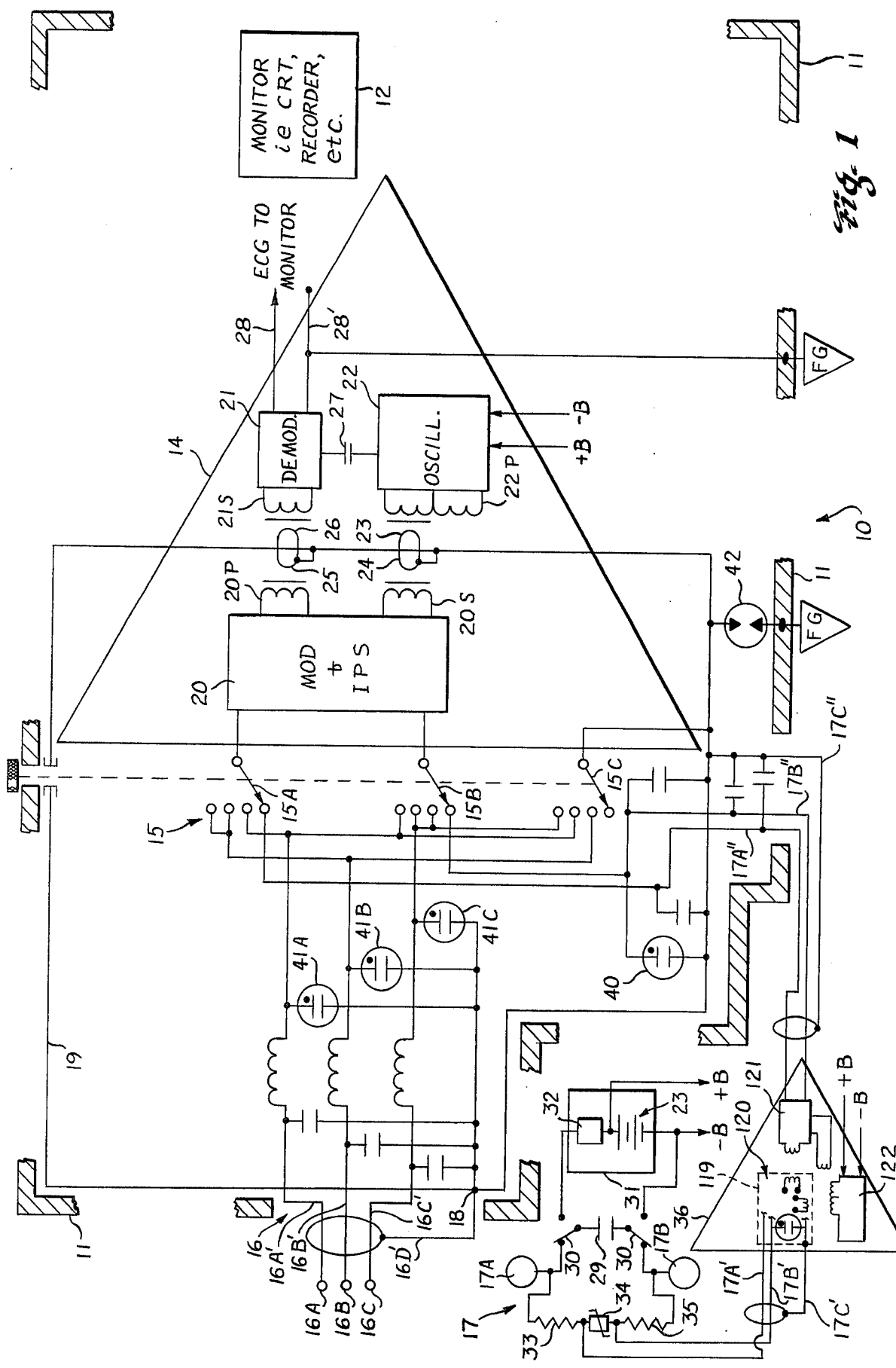
FIG. 1 is a system diagram of a heart defibrillating and monitoring system utilizing the improved isolation means of the invention.
Figure 2:
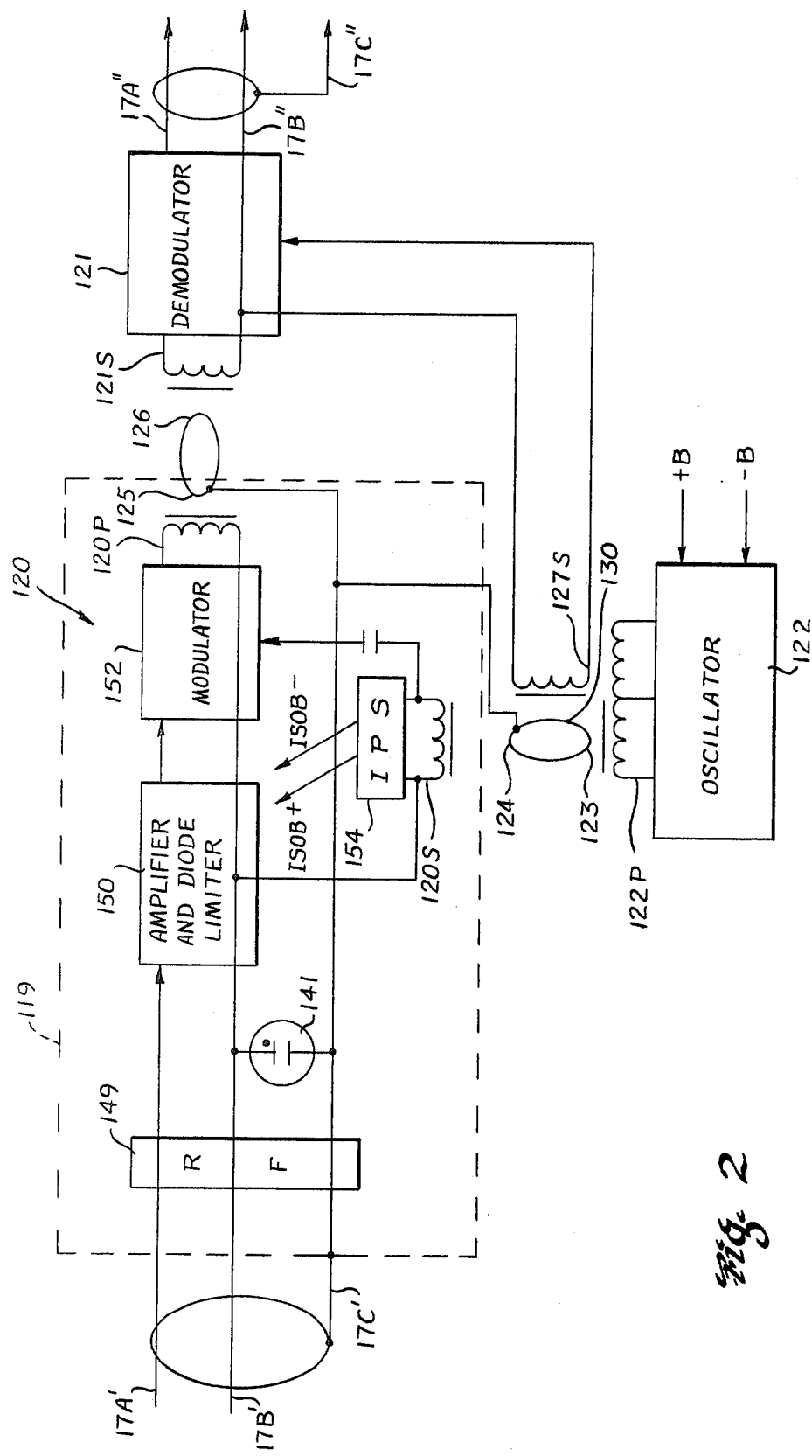
FIG. 2 is a more-detailed block diagram of the isolation amplifier of FIG. 1 providing the improved isolation of the invention.

Referring to FIGS. 1 and 2, there is illustraded in FIG. 1 in generalized form a monitoring system, generally designated 10. The monitoring system 10 may be contained within one or more housings or chasis 11 and include a monitor 12 which receives an ECG signal from the output of an isolation amplifier 14. The input portion of isolation amplifier 14 is electrically isolated and shielded from the output portion thereof and receives input signals via lead selector switch 15. The input signals may be provided by a system of patient electrodes and leads 16 or alternatively by a system of defibrillating electrodes and leads 17. The monitor 12 or monitoring system 10 may be a cathode-ray tube, a permanent recorder, a cardio-tachometer, and/or other means responsive to an electrocardiographic signal. As used herein, the phrase "isolated" is generally intended to mean the ability of ajacent circuits to withstand potential differences there between as great as 10 kilovolts without electrical current flow therebetween.

The patient electrode system 16 is here illustrated as comprising three patient electrodes 16A, 16B and 16C respectively extended to respective contacts on selector switch 15 via patient leads 16A', 16B' and 16C'. A guard or shield lead 16D' is connected to a guard terminal 18 which is electrically connected to and part of a conductive shield box 19. The guard lead 16D' and the shield 19 are at the same potential, and the phrases "guard" and "shield" may be used interchangeably herein.

In the embodiment illustrated, the monitoring system 10 and the defibrillator to be hereinafter described are battery-powered and accordingly, are not normally referenced or directly connected to earth or ground potential. Accordingly, the chassis 11 of monitoring system 10 is represented as being at a so-called floating ground potential and thus not necessarily at actual ground (i.e. earth potential). The electrode system 16 as well as the guard lead 16D' thereof is electrically isolated from the system chassis 11 to provide an isolated input to isolation amplifier 14 via selector switch 15. This isolation is provided to prevent an undesired leakage current flow to a patient who may be connected to electrode systems 16, as described in U.S. Pat. No. 3,946,324 issued Mar. 23, 1976 to L. R. Smith for Isolation Amplifier and in U.S. Patent Application, Ser. No. 757,166 filed Jan. 6, 1977 by George Cavigelli for Isolation Amplifier having Improved Fidelity, which patent and application respectively are incorporated herein by reference. The patient electrodes 16A, 16B and 16C are normally placed at different positions on the patient and serve to develop ECG signal voltages between each pair thereof. The moving contactors 15A and 15B of selector switch 15 comprise of two inputs (high and low) to isolation amplifier 14. Actuation of lead selector switch 15 to any one of its three "uppermost" positions illustrated in FIG. 1 is operative to connect the respective differential patient ECG signal to isolation amplifier 14 from electrode system 16. The fourth, or "lowermost", positioning of the contactors of lead selector switch 15 is operative to connect the input of isolation amplifier 14 with the signal appearing on the defibrillating electrode system 17. A third contactor 15C of lead selector switch 15 is operative to connect certain ones of the patient leads to the shield 19.

The isolation amplifier 14 is generally of the type describe in the aforementioned U.S. Pat. No. 3,946,324 and includes an isolated input section 20, and output section 21 conductively isolated from input section 20 and an oscillator section 22 also isolated from input section 20. The input section 20 typically comprises an amplifier and AC modulator or chopper and an isolated power supply. The oscillator section 22 is powered by DC potentials + B and − B from battery 23, or a second similar battery not shown, and preferrably provides a square wave as disclosed more fully in the aforementioned Application, Ser. No. 757,166. The AC signal from oscillator 22 is transformer-coupled to the modulator section 20 to provide the AC carrier exitation for the modulator and also to energize a rectifier power supply circuit to produce isolated DC voltages for the active elements of the input section. That transformer coupling is provided from transformer primary 22P to transformer secondary 20S by a pair of series connected back-to-back windings 23, 24, each passing through a respective ferrite core (not shown) whereby to complete isolation transformer 22P, 20S.

The modulator of input section 20 converts the DC or slowly variating DC input signal from the patient to a chopped AC signal, the amplitude of which is a function of the input signal amplitude. The AC signal from the modulator appears on transformer primary 20P and is inductively coupled to the transformer secondary 21S of the modulator 21 via a pair of series connected, back-to-back windings 25, 26 each passing through respective ferrite cores (not shown) in the manner previously described.

The square wave signal from oscillator 22 is connected to the demodulator 21 through a series coupling capacitor 27 for controlling the demodulator in phase with the operation of the modulator input section 20. The demodulator 21 is, like the modulator of section 20, effectively a series switch, opened and closed alternately, in synchronism with the carrier of square wave frequency or oscillator 22. The demodulator 21 produces a DC output signal, as represented by line 28, corresponding to the AC amplitude of the modulator square wave, and thereby corresponding to the original DC signal applied to input 15A and 15, but with a moderately higher power level. (The other output terminal 28' from demodulator 21 is typically connected to the floating ground potential of chasis 11.) The coupling circuit between oscillator 22 and demodulator 21 is considered to be limitedly non-conductive, i.e. it will not normally pass DC currents.

In addition to patient electrode system 16, used solely for receiving ECG signals from a patient there is also a defibrillating electrode system 17 which alternatively may provide an ECG signal input to the monitoring system 10 via lead selector switch and isolation amplifier 14. Defibrillator electrode system 17 may be viewed as having its origin with a pair of conventional defibrillator paddles or electrodes 17A and 17B which are capable either of delivering a defibrillating signal for pulse to a patient or for sensing the patient's ECG signals for input to monitoring apparatus 10. The defibrillating signal delivered to the patient in an emergency situation results from the relatively sudden discharge of electrical energy stored in capacitor 29, as by a pair of conventional trigger switches (not shown) in the respective paddle circuits. A switch 30 connected to capacitor 29 is operative in a "charging" mode to connect capacitor 29 across the source 31 of high-voltage energy, which source includes battery 23 and ADC-DC step-up converter 32. Typically, after capacitor 29 is charged to a potential of about 7,000 volts it is capable of delivering a 320 joules defibrillating pulse. After capacitor 29 is charged, switch 30 may be manually or automatically actuated to disconnect capacitor 29 from the charging circuit 31 and to connect it in standby condition (as shown) across paddle 17A, 17B for delivering a 7,000 volt defibrillating pulse thereacross when the trigger switches are concurrently actuated. It will be noted that neither paddle 17A nor paddle 17B is connected to actual ground potential in the circuit as illustrated.

A signal-developing circuit including, in series, fixed resistor 33 varistor 34 and fixed resistor 35, is connected in parallel with capacitor 29 across the defibrillating electrodes 17A, 17B for developing the patient's ECG signal which may then be input by the defibrillating electrode system 17 to the monitoring system 10. Resistors 33 and 35 may typically each have fixed values of 10 Kohm and varistor 34 is of a type which varies its resistance as a function of the applied voltage thereby to limit the magnitude of the signal develop there across. Accordingly, defibrillating electrode system leads 17A' and 17B' are respectively connected to opposite ends of varistor 34 and the voltage difference appearing thereacross forms the ECG signal delivered via the defibrillating electrode system 17 to selector switch 15 and ultimately to isolation amplifier 14.

Leads 17A' and 17B' have previously extended directly and continuously to respective contacts on selector switch 15, and their associate guard electrode 17C' has similarly extended directly and continuously to the shield 19. However, in accordance with the present invention, the signal appearing on the defibrillation electrode system 17 proximate the varistor 34 is isolated from selector switch 15. Similarly, guard electrode 17C' is electrically isolated from shield 19. This isolation is provided by the isolation amplifier 36 inserted in the system intermediate the defibrillation electrode system 17 and the selector switch 15. Accordingly, the signal output leads from isolation amplifier 36 are designated 17A", and 17B", to correspond with input leads 17A' and 17B' respectively. The guard associated with the output of isolation amplifier 36 is accordingly designated 17C" and is connected to shield 19. The function of isolation amplifier 36 will be discussed hereinafter in greater detail; however the present discussion will focus upon the monitoring and defibrillating system prior to insertion of such isolation amplifier.

Under typical circumstances, the defibrillation paddles 17A and 17B are applied at space-apart positions on a patient's body, first for detecting the patient's ECG and subsequently for application of one or more defibrillating pulses thereto. The patient electrodes 16A, 16B, 16C may or may not be applied to the patient's body during efforts to defibrillate, but usually are applied to the patient following defibrillation. With the selector switch 15 in either of the three uppermost positions, the patient leads will provide the input to the monitoring system and alternatively, with the selector switch in the lowermost position the defibrillating leads 17A', 17B' – 17A", 17B" provide the input to the monitoring system. In this latter mode, the signal appearing across leads 17A", 17B" is normally a low voltage value of a patient's ECG and the common-mode voltage across the paddles 17A, 17B is relatively small. However when a defibrillating voltage of about 7,000 volts is applied between paddles 17A and 17B, the common-mode voltage between either paddle and a particular lead 17A' and 17B' may be approximately one-half of 7,000 volts, or 3,500 volts. In such instance, although the differential voltage between leads 17A', 17B' may be only of relatively small value, the common-mode voltage is obviously quite significant.

Because of the structure of selector switch 15, this relatively high common-mode voltage (i.e. 3,500 volts) may normally be impressed across a pair of normally closely-spaced switch contacts. Switch 15 is not designed for high-voltage operation and accordingly, such high potential would result in break down of the air insulator therebetween and electrical arcing and resulting damage to the switch. Therefore, in order to prevent such damage, neon tube 40 is connected between lead 17B" and the guard or shield electrode 19. Similarly, the three neon tubes 41A, 41B and 41C are also connected between the guard electrode 16B' (connected to shield 19) and the patient leads 16A', 16B' and 16C' respectively prior to their junction with the contacts of selector switch 15. Neon tubes 40, 41A, 41B and 41C are non-conductive for potentials there across below some threshold value and break down and conduct when the threshold potential is exceeded. Typically, the neon tubes of the present embodiment have a threshold potential of about 80 volts.

Therefore, when the common-mode voltage appearing on the defibrillating electrode system 17 exceeds 80 volts, as during a defibrillation pulse, neon tube 40 breaks down and provides a conductive path therethrough, thereby preventing arcing at the selector switch 15. Neon tubes 41A, 41B, and 41C operate in a similar manner if such high voltage is impressed on the patient electrode system 16. It will be appreciated that the breakdown voltage may be as high as 160 volts if the particular high potential is impressed across any two of leads 16A, 16B and 16C in as much as two of the neon bulbs 41A, 41B and 41C are then placed in series. The neon tubes 41A, 41B and 41C are necessitated by the possibility of a high voltage being impressed across any pair of leads in the patient electrode system 16. Thus it will be seen that neon tube 40 and tubes 41A, 41B and 41C effectively protect the selector switch 15. A radio frequency filter, comprised of a shunt capacitor to the guard lead 16D and a series inductor, is inserted in each of the patient leads 16A, 16B and 16C prior to junction with neon tubes 41A, 41B and 41C for preventing the input of radio frequency signal voltages to the system 10. Similarly, shunt capacitances to guard lead 17C" from defibrillating electrode leads 17A" and 17B" respectively, also serve to suppress radio frequency inputs to system 11.

Additional protection for the circuitry is afforded by spark gap 42 which is connected between the shield 19 and the system chassis 11. Normally both the shield 19, and the chassis 11 have floating potentials a large potential gradient between the two is not developed; however, in the event one or the other of those elements is prevented from floating, by being connected to actual ground through contact with some foreign object, the spacing between those elements may be sufficiently small to permit arcing with its attendant destructive effect. Accordingly, to prevent such arcing, the spark gap 42 breaks down at potentials exceeding 800 volts, thereby preventing random destructive arcing between chassis 11 and shield 19.

During use of the paddles 17A, 17B for defibrillating a patient one of the paddles may be positioned on the patient such that it is at or very near actual ground potential in as much as that portion of the patient is in contact with actual ground potential. In such instance the common-mode voltage appearing at input leads 17A', 17B' will be approximately 3,500 volts different (plus or minus) from actual ground potential. Accordingly, if a generally conductive, foreign object is at or near actual ground potential and comes into contact with any of the electrodes or leads of patient electrode system 16, such system will then be substantially at ground potential and a conductive path will be established by breakdown of neon tube 40 and one or more of neon tubes 41A, 41B, 41C when the total potential difference there across exceeds about 160 volts. For such conduction, the shield 19 serves as a common conductor between the patient electrode system 16 and the defibrillating electrode system 17. The resulting conduction and development of a leakage current through the circuitry and the foreign object is generally undesirable, and the addition of isolation amplifier 36 serves to prevent this condition.

Isolation amplifier 36, illustrated in greater detail in FIG. 2, is in most respects identical to the isolation amplifier 14 previously described. It includes an input section 120, an output section 121, and an oscillator 122. The input section 120 is electrically isolated and floating relative to the output, as represented by the dotted shield structure 119. For the purposes of convenience, the radio frequency suppression circuitry 149 of amplifier 36 has been shown as a part of the amplifier itself, whereas it preceded selector switch 15 relative to the amplifier 14 in FIG. 1. Similarly, a neon tube 141 analogous in function to tubes 41A, 41B or 41C of FIG. 1, is connected between defibrillating lead 17B' and the respective guard electrode 17C'. As with input section 20, the input section 120 of amplifier 36 includes an amplifier and diode limitor 150 which receives and amplifies the signal appearing between leads 17A' - 17B' and provides an input to a chopper or modulator 152 which develops the output AC signal across transformer primary 120P. Positive and negative isolated DC supply potentials, ISOB+ and ISOB− are provided by an isolated power supply 154 which receives, through transformer secondary 120S, AC square wave energy inductively coupled thereto from the transformer primary 122P of square wave oscillator 122. The transformer coupling is provided from transformer primary 122P to transformer secondary 120S by a pair of series connected, back-to-back windings 123 and 124 each passing through a respective ferrite core as earlier described.

However, in accordance with a further aspect of the invention, transformer primary 122P additionally delivers AC square wave energy to demodulator 121 through a transformer secondary 127S rather than through the coupling capacitor 27 described in relation to isolation amplifier 14 in FIG. 1. The AC square wave energy from transformer primary 122P is inductively coupled to transformer secondary 127S by a third winding 130 connected in series with the pair of winding 123 and 124 and also passing through a respective ferrite core. Accordingly, it will be observed that there is no direct conductive coupling between the output section 121 and the oscillator 122 of isolation amplifier 36, for a purpose to be hereinafter described.

The AC signal appearing across transformer 120P from modulator 152 is transformer-coupled to the transformer secondary 121S associated with the demodulator of output section 121. The transformer coupling is provided from transformer primary 120P to transformer secondary 121S by a pair of series connected back-to-back windings 125, 126, each passing through a respective ferrite core wherby to complete isolation transformer 120P, 121S.

As with isolation amplifier 14, the DC signal developed across output leads 17A" - 17B" is isolated from the signal and circuitry associated with the input of isolation amplifier 36. Even though a grounded foreign object contacting any portion of the patient electrode system 16 may place that system at actual ground potential, a 3,500 volt common-mode voltage appearing at the input of isolation amplifier 36 is prevented from appearing at the isolated modulator output 121 thereof. Accordingly, the ground potential on patient electrode system 16 will be reflected at the demodulator 121 without forcing a breakdown of neon tube 40 and at least one of tubes 41A, 41B, 41C. Thus, this type of leakage current is prevented during a defibrillating pulse, even though the patient electrode system 16 may be directly connected to ground potential. It should be appreciated that the isolating effect of isolation amplifier 36 responsible for this mode of protection might also be obtained from an isolation amplifier of the type such as 14 in FIG. 1, where oscillator 22 and demodulator 21 are capacitively coupled to one another, the requiste degree of isolation being between the modulator 20 and the demodulator 21.

In addition to the aforementioned mode of current leakage caused by the grounding of electrode system 16 and generally prevented by the insertion of an isolation amplifier between defibrillating electrode system 17 and the selector switch 15, there is another condition which may give rise to unwanted and possibly destructive leakage current through the isolation amplifier (36) located in the defibrillating electrode system 17. More particularly, in the event one of the defibrillating paddles 17A, 17B is placed on a patient substantially in contact with actual ground potential and the other paddle is placed quite near or in contact with one of the electrode of patient electrode system 16 contrary to good operating practice, the entire defibrillating pulse potential (i.e. 7,000 volts) will then be impressed on patient electrode system 16 and thus also on the output of the isolation amplifier 36. In the event isolation amplifier 36 was of a design similar to that of isolation amplifier 14 in which the oscillator and the demodulator portion were capacitively coupled to one another, and the DC supply (+B and −B) for the oscillator was relative near ground potential as determined by one of paddles 17A, 17B its self being at ground potential, the full 7,000 volt defibrillating potential would be impressed across the demodulator and oscillator circuitry. The limited non-conductivity of the coupling capacitor between the demodulator and oscillator would be rendered useless by the extremely high potential and to some extent also by the pulseatile characteristic of the defibrillation pulse. Clearly, the circuitry of the demodulator and oscillator are not intended to withstand the resulting current flow occasioned by impressing such a high potential across them and the then generally-conductive capacitor link therebetween, and accordingly, damage to or destruction of those circuits may result.

However, as a further aspect of the present invention, the demodulator 121 and the oscillator 122 of isolation amplifier 36 are isolated from one another to prevent such circuit-damaging leakage current from occurring. This isolation is effected by transformer-coupling the AC square wave from oscillator 122 to the demodulator 121 via the isolation transformer comprised of primary winding 122P and secondary winding 127S. The secondary winding 127S is operatively connected to the gate electrode of a FET (not shown) which serves as the demodulator 121. In this way, not only are modulator 121 and oscillator 122 each isolated from input section 120 (modulator 152), but also oscillator 122 and demodulator 121 are isolated from one another. Although the concept of isolating the demodulator from the oscillator is not unknown, as evidenced by U.S. Pat. No. 3,156,859 issued Nov. 10, 1964 to J. A. Cox for Shielded Direct Current Amplifier, such circuits have generally not been of the type intended for use in high-voltage environments and certainly have not been considered for application in defibrillating and monitoring systems such as disclosed herein.

Thus, should a 7,000 volt defibrillating signal be inadvertently impressed on the patient electrode system 16, the output of the modulator 121 is able to float to that level of potential and the oscillator 122 may safely remain in the proximity of actual ground potential without damaging that circuitry of amplifier 36.

A still further advantage is attained with the present embodiment by placing isolation amplifier 36 in the defibrillating electrode system, particularly if the input to the isolating amplifier is relatively proximate resistors 33, 35 and varistor 34. This advantage obtains because the normally long run of electrode system 17 is one of high impedance and thus susceptible to more pick-up. However, the addition of amplifier 36 shortens the high impedance pathlength and replaces it with a much less susceptible to more low impedance path.

It will be appreciated that the advantages obtained by inserting the isolation amplifier 36 in the system in the manner described will similarly extend to line-operated (as opposed to battery-operated) systems in which the chassis are normally connected to actual ground. In fact, in a line-operated system the isolation between oscillator 122 and demodulator 121 of isolation amplifier 36 is required in order to preserve the patient isolation initially afforded by isolation amplifier 14.

The invention may be embodied in other specific forms without departing from the spirit or essential characteristics thereof. The present embodiments are therefore to be considered in all aspects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a heart defibrillating and monitoring system having a source of high-voltage defibrillating signals and signal monitoring means for monitoring signals indicating heart activity, a first electrode system for selectively applying defibrillating signals to a patient and for selectively applying monitoring signals to the means for monitoring signals, and a second electrode system for selectively applying monitoring signals to the means for monitoring signals, said means for monitoring signals include a first isolation amplifier, switch means for selectively applying monitoring signals to said first isolation amplifier alternatively from said first electrode system or from said second electrode system, the improvement comprising a second isolation amplifier coupled intermediate said first electrode system and said switch means, whereby to prevent current leakage between said first electrode system and said second electrode system during application of a defibrillating signal.

2. The heart defibrillating and monitoring system of claim 1, wherein said second isolation amplifier comprises three separate mutually conductively isolated sections including an input section having an AC modulator, an output section having a demodulator and an oscillator section, said modulator being isolated from said demodulator and, thereby to also prevent a current path from said first electrode system through said second electrode system and said second isolation amplifier demodulator section and oscillator section in the event a high defibrillating signal potential is applied to said second electrode system, said oscillator section being conductively isolated from said AC modulator and from said demodulator.

3. The heart defibrillating and monitoring system of claim 1, wherein said defibrillating and monitoring system is battery powered and normally has only a floating ground.

4. The heart defibrillating and monitoring system of claim 1, wherein the first electrode system and the second electrode system are each connected to a common guard conductor through respective threshold discharge devices, said threshold discharge devices being operative to isolate said respective electrode systems from said common guard conductor only so long as the electrical potential there across is less than a predetermined threshold value, said predetermined threshold value being substantially less than the potential of a defibrillating signal.

5. The heart defibrillating and monitoring system of claim 2, wherein the first electrode system and the second electrode system are each connected to a common guard conductor through respective threshold discharge devices, said threshold discharge devices being operative to isolate said respective electrode systems from said common guard conductor only so long as the electrical potential there across is less than a predetermined threshold value, said predetermined threshold value being substantially less than the potential of a defibrillating signal.

6. The heart defibrillating and monitoring system of claim 4, wherein said defibrillating and monitoring system is battery powered and normally has only a floating ground.

7. The heart defibrillating and monitoring system of claim 4, including means for normally isolating said common guard conductor from actual ground potential.

* * * * *